United States Patent
Pett

(10) Patent No.: US 12,402,911 B2
(45) Date of Patent: Sep. 2, 2025

(54) ASPIRATION APPARATUS FOR INTRAOSSEOUS ACCESS SYSTEM

(71) Applicant: Bard Access Systems, Inc., Salt Lake City, UT (US)

(72) Inventor: Daniel Pett, Sandy, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 348 days.

(21) Appl. No.: 17/469,613

(22) Filed: Sep. 8, 2021

(65) Prior Publication Data

US 2022/0071659 A1 Mar. 10, 2022

Related U.S. Application Data

(60) Provisional application No. 63/076,189, filed on Sep. 9, 2020.

(51) Int. Cl.
| | |
|---|---|
| *A61B 17/34* | (2006.01) |
| *A61B 17/00* | (2006.01) |
| *A61B 17/16* | (2006.01) |

(52) U.S. Cl.
CPC ...... *A61B 17/3472* (2013.01); *A61B 17/1628* (2013.01); *A61B 17/164* (2013.01);
(Continued)

(58) Field of Classification Search
CPC ............ A61B 17/3472; A61B 17/1628; A61B 17/164; A61N 2017/00477; A61N 2217/005
See application file for complete search history.

(56) References Cited

U.S. PATENT DOCUMENTS

| | | |
|---|---|---|
| 2,773,501 A | 12/1956 | Young |
| 3,071,135 A | 1/1963 | Baldwin et al. |

(Continued)

FOREIGN PATENT DOCUMENTS

| | | |
|---|---|---|
| CN | 108742795 A | 11/2018 |
| CN | 110547847 A | 12/2019 |

(Continued)

OTHER PUBLICATIONS

Ekchian Gregory James et al: "Quantitative Methods for In Vitro and In Vivo Characterization of Cell and Tissue Metabolism", Jun. 11, 2018, XP055839281, retrieved from the internet on Sep. 8, 2021 : URL: https://dspace.mit.edu/bitstream/handle/1721.1/117890/1051211749-MIT.pdf?sequence=1&isAllowed=y.

(Continued)

*Primary Examiner* — Nathan R Price
*Assistant Examiner* — Mark A Igel
(74) *Attorney, Agent, or Firm* — Rutan & Tucker LLP

(57) ABSTRACT

Embodiments disclosed herein are directed to an intraosseous access system configured to confirm access to a medullary cavity. The system includes a driver housing, an access system including a drive train, a needle assembly rotatably coupled to the access system, and an aspiration system. The needle assembly can include a needle defining a lumen and an obturator disposed therein. The aspiration system can include a syringe or a vacutainer, coupled to the obturator. Sliding one of a plunger or a vacutainer proximally can withdraw the obturator from the needle lumen and place a vacuum in fluid communication with the needle lumen to draw a fluid flow therethrough. A portion of the aspiration system can rotate along with the needle assembly. Withdrawing the obturator can place the obturator within the syringe or the vacutainer mitigating needle stick injuries. If (Continued)

the medullary cavity has not been accessed, the obturator can be replaced.

11 Claims, 4 Drawing Sheets

(52) U.S. Cl.
CPC ............... *A61B 2017/00477* (2013.01); *A61B 2217/005* (2013.01)

(56) References Cited

U.S. PATENT DOCUMENTS

| | | | |
|---|---|---|---|
| 3,261,594 A * | 7/1966 | Michel | B01F 31/201 |
| | | | 366/202 |
| 3,734,207 A * | 5/1973 | Fishbein | A61B 17/1622 |
| | | | 173/217 |
| 3,753,432 A * | 8/1973 | Guerra | A61B 5/154 |
| | | | 600/577 |
| 3,804,544 A | 4/1974 | Adams | |
| 3,811,442 A * | 5/1974 | Maroth | A61M 5/20 |
| | | | 604/188 |
| 3,815,605 A | 6/1974 | Schmidt et al. | |
| 3,991,765 A | 11/1976 | Cohen | |
| 4,266,555 A | 5/1981 | Jamshidi | |
| 4,314,565 A | 2/1982 | Lee | |
| 4,342,724 A * | 8/1982 | Narra | B01L 3/5021 |
| | | | 422/918 |
| 4,381,777 A * | 5/1983 | Garnier | A61M 5/20 |
| | | | 604/188 |
| 4,383,530 A | 5/1983 | Bruno | |
| 4,562,844 A * | 1/1986 | Carpenter | A61B 5/150244 |
| | | | 604/220 |
| 4,736,742 A | 4/1988 | Alexson et al. | |
| 4,787,893 A * | 11/1988 | Villette | A61C 19/08 |
| | | | 604/188 |
| 4,889,529 A | 12/1989 | Haindl | |
| 4,952,207 A | 8/1990 | Lemieux | |
| 4,964,854 A | 10/1990 | Luther | |
| 4,969,870 A | 11/1990 | Kramer et al. | |
| 5,040,542 A | 8/1991 | Gray | |
| 5,042,558 A | 8/1991 | Hussey et al. | |
| 5,053,017 A | 10/1991 | Chamuel | |
| 5,122,114 A | 6/1992 | Miller et al. | |
| 5,207,697 A | 5/1993 | Carusillo et al. | |
| 5,263,939 A | 11/1993 | Wortrich | |
| 5,290,267 A | 3/1994 | Zimmermann | |
| 5,312,364 A | 5/1994 | Jacobs | |
| 5,332,398 A | 7/1994 | Miller et al. | |
| 5,364,367 A | 11/1994 | Banks et al. | |
| 5,372,583 A | 12/1994 | Roberts et al. | |
| 5,384,103 A * | 1/1995 | Miller | A61L 2/26 |
| | | | 206/508 |
| 5,406,940 A | 4/1995 | Melzer et al. | |
| 5,451,210 A | 9/1995 | Kramer et al. | |
| 5,554,154 A | 9/1996 | Rosenberg | |
| 5,573,358 A | 11/1996 | Gobbers et al. | |
| 5,575,780 A | 11/1996 | Saito | |
| 5,591,188 A | 1/1997 | Waisman | |
| 5,601,559 A | 2/1997 | Melker et al. | |
| 5,667,509 A | 9/1997 | Westin | |
| 5,688,249 A | 11/1997 | Chang et al. | |
| 5,694,019 A | 12/1997 | Uchida et al. | |
| 5,779,708 A | 7/1998 | Wu | |
| 5,817,052 A | 10/1998 | Johnson et al. | |
| 5,853,393 A | 12/1998 | Bogert | |
| 5,868,711 A | 2/1999 | Kramer et al. | |
| 5,885,293 A | 3/1999 | McDevitt | |
| 5,927,976 A | 7/1999 | Wu | |
| 5,960,797 A | 10/1999 | Kramer et al. | |
| 5,967,143 A | 10/1999 | Klappenberger | |
| 6,018,227 A | 1/2000 | Kumar et al. | |
| 6,056,165 A * | 5/2000 | Speranza | B05C 17/0103 |
| | | | 222/326 |
| 6,104,162 A | 8/2000 | Sainsbury et al. | |
| 6,117,108 A | 9/2000 | Woehr et al. | |
| 6,135,769 A | 10/2000 | Kwan | |
| 6,159,161 A * | 12/2000 | Hodosh | A61M 5/20 |
| | | | 600/561 |
| 6,199,664 B1 | 3/2001 | Tkaczyk et al. | |
| 6,210,373 B1 | 4/2001 | Allmon | |
| 6,228,088 B1 | 5/2001 | Miller et al. | |
| 6,247,928 B1 | 6/2001 | Meller et al. | |
| 6,270,484 B1 | 8/2001 | Yoon | |
| 6,273,715 B1 | 8/2001 | Meller et al. | |
| 6,419,490 B1 | 7/2002 | Kitchings Weathers, Jr. | |
| 6,458,117 B1 | 10/2002 | Pollins, Sr. | |
| 6,527,778 B2 | 3/2003 | Athanasiou et al. | |
| 6,547,561 B2 * | 4/2003 | Meller | A61C 1/081 |
| | | | 433/80 |
| 6,602,214 B2 | 8/2003 | Heinz et al. | |
| 6,626,887 B1 | 9/2003 | Wu | |
| 6,629,959 B2 | 10/2003 | Kuracina et al. | |
| 6,641,395 B2 | 11/2003 | Kumar et al. | |
| 6,652,490 B2 | 11/2003 | Howell | |
| 6,692,471 B2 | 2/2004 | Boudreaux | |
| 6,715,969 B2 | 4/2004 | Eriksen | |
| 6,761,726 B1 | 7/2004 | Findlay et al. | |
| 6,814,734 B2 | 11/2004 | Chappuis et al. | |
| 6,830,562 B2 | 12/2004 | Mogensen et al. | |
| 6,875,219 B2 | 4/2005 | Arramon et al. | |
| 6,905,486 B2 | 6/2005 | Gibbs | |
| 6,916,292 B2 | 7/2005 | Morawski et al. | |
| 6,984,213 B2 | 1/2006 | Horner et al. | |
| 6,997,907 B2 | 2/2006 | Safabash et al. | |
| 7,112,191 B2 | 9/2006 | Daga | |
| 7,135,031 B2 | 11/2006 | Flint | |
| 7,214,208 B2 | 5/2007 | Vaillancourt et al. | |
| 7,347,838 B2 | 3/2008 | Kulli | |
| 7,347,840 B2 | 3/2008 | Findlay et al. | |
| 7,407,493 B2 | 8/2008 | Cane' | |
| 7,458,954 B2 | 12/2008 | Ferguson et al. | |
| 7,513,888 B2 | 4/2009 | Sircom et al. | |
| 7,530,965 B2 | 5/2009 | Villa et al. | |
| 7,534,227 B2 | 5/2009 | Kulli | |
| 7,569,033 B2 | 8/2009 | Greene et al. | |
| 7,582,102 B2 | 9/2009 | Heinz et al. | |
| 7,588,559 B2 | 9/2009 | Aravena et al. | |
| 7,658,725 B2 | 2/2010 | Bialecki et al. | |
| 7,670,328 B2 | 3/2010 | Miller | |
| 7,699,807 B2 | 4/2010 | Faust et al. | |
| 7,699,850 B2 | 4/2010 | Miller | |
| 7,736,332 B2 | 6/2010 | Carlyon et al. | |
| 7,749,225 B2 | 7/2010 | Chappuis et al. | |
| 7,798,994 B2 | 9/2010 | Brimhall | |
| 7,811,260 B2 * | 10/2010 | Miller | A61M 5/1454 |
| | | | 604/188 |
| 7,815,642 B2 | 10/2010 | Miller | |
| 7,828,774 B2 | 11/2010 | Harding et al. | |
| 7,833,204 B2 | 11/2010 | Picha | |
| 7,842,038 B2 | 11/2010 | Haddock et al. | |
| 7,850,620 B2 * | 12/2010 | Miller | A61B 50/33 |
| | | | 600/568 |
| 7,850,650 B2 | 12/2010 | Breitweiser | |
| D633,199 S | 2/2011 | MacKay et al. | |
| 7,899,528 B2 | 3/2011 | Miller et al. | |
| 7,905,857 B2 | 3/2011 | Swisher | |
| 7,951,089 B2 * | 5/2011 | Miller | A61B 17/3476 |
| | | | 600/568 |
| 7,955,297 B2 | 6/2011 | Radmer et al. | |
| 7,972,339 B2 | 7/2011 | Nassiri et al. | |
| 7,976,502 B2 | 7/2011 | Baid | |
| 8,038,038 B2 * | 10/2011 | Hillhouse | B05B 11/1095 |
| | | | 185/39 |
| 8,038,664 B2 | 10/2011 | Miller et al. | |
| 8,043,253 B2 | 10/2011 | Kraft et al. | |
| 8,043,265 B2 | 10/2011 | Abe et al. | |
| 8,142,365 B2 | 3/2012 | Miller | |
| 8,152,771 B2 | 4/2012 | Mogensen et al. | |
| 8,162,904 B2 | 4/2012 | Takano et al. | |
| 8,167,899 B2 | 5/2012 | Justis et al. | |
| 8,221,398 B2 | 7/2012 | Isobe et al. | |
| 8,235,945 B2 | 8/2012 | Baid | |

(56) References Cited

U.S. PATENT DOCUMENTS

| | | |
|---|---|---|
| 8,246,584 B2 | 8/2012 | Aravena et al. |
| 8,273,053 B2 | 9/2012 | Saltzstein |
| 8,292,891 B2 | 10/2012 | Browne et al. |
| 8,308,693 B2 | 11/2012 | Miller et al. |
| 8,333,769 B2 | 12/2012 | Browne et al. |
| 8,356,598 B2 | 1/2013 | Rumsey |
| 8,357,163 B2 | 1/2013 | Sidebotham et al. |
| 8,388,541 B2 | 3/2013 | Messerly et al. |
| 8,388,623 B2 | 3/2013 | Browne et al. |
| 8,414,539 B1 | 4/2013 | Kuracina et al. |
| 8,419,683 B2 | 4/2013 | Miller et al. |
| 8,480,632 B2 | 7/2013 | Miller et al. |
| 8,480,672 B2 | 7/2013 | Browne et al. |
| 8,486,027 B2 | 7/2013 | Findlay et al. |
| 8,506,568 B2 | 8/2013 | Miller |
| 8,535,271 B2 | 9/2013 | Fuchs et al. |
| 8,562,615 B2 | 10/2013 | Browne et al. |
| 8,641,715 B2 | 2/2014 | Miller |
| 8,647,257 B2 | 2/2014 | Jansen et al. |
| 8,656,929 B2 | 2/2014 | Miller et al. |
| 8,657,790 B2 | 2/2014 | Tal et al. |
| 8,663,231 B2 | 3/2014 | Browne et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,771,230 B2 | 7/2014 | White et al. |
| 8,781,555 B2 | 7/2014 | Burnside et al. |
| 8,801,663 B2 | 8/2014 | Woehr |
| 8,812,101 B2 | 8/2014 | Miller et al. |
| 8,814,835 B2 | 8/2014 | Baid |
| 8,821,493 B2 | 9/2014 | Anderson |
| 8,828,001 B2 | 9/2014 | Stearns et al. |
| 8,849,382 B2 | 9/2014 | Cox et al. |
| 8,870,872 B2 | 10/2014 | Miller |
| 8,894,654 B2 | 11/2014 | Anderson |
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,149,625 B2 | 10/2015 | Woehr et al. |
| 9,173,679 B2 | 11/2015 | Tzachar et al. |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,445,743 B2 | 9/2016 | Kassab |
| 9,451,968 B2 | 9/2016 | Miller et al. |
| 9,451,983 B2 | 9/2016 | Windolf |
| 9,456,766 B2 | 10/2016 | Cox et al. |
| 9,480,483 B2 | 11/2016 | Browne et al. |
| 9,492,097 B2 | 11/2016 | Wilkes et al. |
| 9,504,477 B2 | 11/2016 | Miller et al. |
| 9,521,961 B2 | 12/2016 | Silverstein et al. |
| 9,545,243 B2 | 1/2017 | Miller et al. |
| 9,554,716 B2 | 1/2017 | Burnside et al. |
| 9,615,816 B2 | 4/2017 | Woodard |
| 9,615,838 B2 | 4/2017 | Nino et al. |
| 9,623,210 B2 | 4/2017 | Woehr |
| 9,636,031 B2 | 5/2017 | Cox |
| 9,636,484 B2 | 5/2017 | Baid |
| 9,649,048 B2 | 5/2017 | Cox et al. |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,782,546 B2 | 10/2017 | Woehr |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 10,052,111 B2 | 8/2018 | Miller et al. |
| 10,092,320 B2 | 10/2018 | Morgan et al. |
| 10,092,706 B2 * | 10/2018 | Denzer ............... A61M 5/50 |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| D898,908 S * | 10/2020 | Denzer .................. D24/127 |
| 10,893,887 B2 | 1/2021 | Blanchard |
| 10,973,532 B2 * | 4/2021 | Miller ............... A61B 10/025 |
| 10,973,545 B2 * | 4/2021 | Miller .............. A61B 17/3474 |
| 10,980,522 B2 | 4/2021 | Muse |
| 11,298,202 B2 * | 4/2022 | Miller ............... A61B 10/025 |
| 11,446,112 B2 * | 9/2022 | Fink ................... A61M 5/427 |
| 11,896,264 B2 | 2/2024 | Lindekugel et al. |
| 11,925,361 B2 | 3/2024 | Pett et al. |
| 12,274,469 B2 * | 4/2025 | Pett .................. A61B 17/3472 |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0010236 A1 * | 1/2004 | Morawski ............ A61B 10/025 |
| | | 604/272 |
| 2004/0059317 A1 | 3/2004 | Hermann |
| 2004/0220497 A1 | 11/2004 | Findlay et al. |
| 2004/0243135 A1 | 12/2004 | Koseki |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0131345 A1 | 6/2005 | Miller |
| 2005/0165403 A1 | 7/2005 | Miller |
| 2006/0015066 A1 | 1/2006 | Turieo et al. |
| 2006/0020191 A1 * | 1/2006 | Brister ............... A61B 5/14532 |
| | | 600/345 |
| 2006/0025723 A1 | 2/2006 | Ballarini |
| 2006/0058826 A1 | 3/2006 | Evans et al. |
| 2006/0147283 A1 | 7/2006 | Phillips |
| 2007/0049945 A1 | 3/2007 | Miller |
| 2007/0096690 A1 | 5/2007 | Casalena et al. |
| 2007/0098507 A1 | 5/2007 | Whitehead |
| 2007/0151116 A1 * | 7/2007 | Malandain .......... A61B 17/0218 |
| | | 33/512 |
| 2007/0191772 A1 | 8/2007 | Wojcik |
| 2007/0270775 A1 | 11/2007 | Miller et al. |
| 2007/0276352 A1 | 11/2007 | Crocker et al. |
| 2007/0282344 A1 | 12/2007 | Yedlicka et al. |
| 2008/0015467 A1 * | 1/2008 | Miller ................ A61B 17/3476 |
| | | 600/568 |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0000292 A1 * | 1/2009 | Schifferer ............. B66F 17/003 |
| | | 702/41 |
| 2009/0022557 A1 | 1/2009 | Whitehead |
| 2009/0048575 A1 | 2/2009 | Waters |
| 2009/0054808 A1 | 2/2009 | Miller |
| 2009/0093830 A1 | 4/2009 | Miller |
| 2009/0194446 A1 | 8/2009 | Miller et al. |
| 2009/0204024 A1 | 8/2009 | Miller |
| 2009/0306697 A1 | 12/2009 | Fischvogt |
| 2010/0004606 A1 | 1/2010 | Hansen et al. |
| 2010/0174243 A1 | 7/2010 | McKay |
| 2010/0202842 A1 | 8/2010 | Whitehead et al. |
| 2010/0204649 A1 | 8/2010 | Miller et al. |
| 2010/0286607 A1 | 11/2010 | Saltzstein |

(56) References Cited

U.S. PATENT DOCUMENTS

| | | |
|---|---|---|
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2011/0202065 A1 | 8/2011 | Takizawa et al. |
| 2012/0116390 A1* | 5/2012 | Madan .................. A61B 50/30 606/41 |
| 2012/0116394 A1* | 5/2012 | Timm .................... G16H 20/40 606/41 |
| 2012/0202180 A1 | 8/2012 | Stock et al. |
| 2012/0203154 A1 | 8/2012 | Tzachar |
| 2012/0274280 A1 | 11/2012 | Yip et al. |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2014/0031674 A1 | 1/2014 | Newman et al. |
| 2014/0031794 A1 | 1/2014 | Windolf |
| 2014/0039400 A1 | 2/2014 | Browne et al. |
| 2014/0081281 A1 | 3/2014 | Felder |
| 2014/0142577 A1 | 5/2014 | Miller |
| 2014/0171873 A1 | 6/2014 | Mark |
| 2014/0188133 A1 | 7/2014 | Misener |
| 2014/0221970 A1* | 8/2014 | Eaton .................. A61M 5/3202 141/2 |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276471 A1 | 9/2014 | Emery et al. |
| 2014/0276833 A1 | 9/2014 | Larsen et al. |
| 2014/0276839 A1 | 9/2014 | Forman et al. |
| 2014/0343454 A1 | 11/2014 | Miller et al. |
| 2014/0343497 A1 | 11/2014 | Baid |
| 2015/0011941 A1 | 1/2015 | Saeki |
| 2015/0025311 A1* | 1/2015 | Kadan ................ A61B 17/3474 600/104 |
| 2015/0045732 A1 | 2/2015 | Murphy et al. |
| 2015/0080762 A1 | 3/2015 | Kassab et al. |
| 2015/0126931 A1 | 5/2015 | Holm et al. |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2015/0367487 A1 | 12/2015 | Nino et al. |
| 2016/0009812 A1* | 1/2016 | Satelli ................... A61P 35/00 424/1.49 |
| 2016/0022282 A1 | 1/2016 | Miller et al. |
| 2016/0022284 A1 | 1/2016 | Lele et al. |
| 2016/0039916 A1* | 2/2016 | Jiang .................... A61P 25/28 435/254.11 |
| 2016/0058432 A1 | 3/2016 | Miller |
| 2016/0066954 A1 | 3/2016 | Miller et al. |
| 2016/0136410 A1 | 5/2016 | Aklog et al. |
| 2016/0183974 A1 | 6/2016 | Miller |
| 2016/0184509 A1 | 6/2016 | Miller et al. |
| 2016/0235949 A1 | 8/2016 | Baid |
| 2016/0305497 A1 | 10/2016 | Victor et al. |
| 2016/0354539 A1 | 12/2016 | Tan et al. |
| 2016/0361519 A1 | 12/2016 | Teoh et al. |
| 2017/0020533 A1* | 1/2017 | Browne ................ A61M 5/158 |
| 2017/0020560 A1 | 1/2017 | Van Citters et al. |
| 2017/0021138 A1 | 1/2017 | Sokolski |
| 2017/0043135 A1 | 2/2017 | Knutsson |
| 2017/0105763 A1 | 4/2017 | Karve et al. |
| 2017/0136217 A1 | 5/2017 | Riesenberger et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0231644 A1 | 8/2017 | Anderson |
| 2017/0303962 A1 | 10/2017 | Browne et al. |
| 2017/0303963 A1 | 10/2017 | Kilcoin et al. |
| 2018/0049772 A1 | 2/2018 | Brockman et al. |
| 2018/0092662 A1 | 4/2018 | Rioux et al. |
| 2018/0116551 A1 | 5/2018 | Newman et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0153474 A1 | 6/2018 | Aeschlimann et al. |
| 2018/0154112 A1 | 6/2018 | Chan et al. |
| 2018/0221003 A1 | 8/2018 | Hibner et al. |
| 2018/0228509 A1* | 8/2018 | Fojtik ................ A61B 17/3472 |
| 2018/0242982 A1 | 8/2018 | Laughlin et al. |
| 2019/0009398 A1 | 1/2019 | Zhong et al. |
| 2019/0030701 A1 | 1/2019 | Duggan |
| 2019/0059986 A1 | 2/2019 | Shelton, IV et al. |
| 2019/0069812 A1 | 3/2019 | Isaacson et al. |
| 2019/0083753 A1 | 3/2019 | Chu |
| 2019/0150954 A1 | 5/2019 | Xie |
| 2019/0175220 A1 | 6/2019 | Coppedge et al. |
| 2019/0282244 A1 | 9/2019 | Muse |
| 2020/0054347 A1* | 2/2020 | Coppedge .......... A61B 17/1628 |
| 2020/0054410 A1 | 2/2020 | Pfotenhauer et al. |
| 2020/0113584 A1* | 4/2020 | McGinley .......... A61B 17/1622 |
| 2020/0129186 A1 | 4/2020 | Miller et al. |
| 2020/0197121 A1 | 6/2020 | Morey et al. |
| 2020/0297382 A1* | 9/2020 | Coppedge .......... A61B 17/3472 |
| 2020/0297452 A1* | 9/2020 | Coppedge .......... A61B 17/1622 |
| 2020/0337782 A1 | 10/2020 | Glassman et al. |
| 2021/0015529 A1* | 1/2021 | Fenton, Jr. ......... A61B 17/8847 |
| 2021/0093357 A1 | 4/2021 | Pett et al. |
| 2021/0093358 A1 | 4/2021 | Lindekugel et al. |
| 2021/0113251 A1* | 4/2021 | Vogt .................. A61M 5/16881 |
| 2021/0282812 A1 | 9/2021 | Tierney et al. |
| 2021/0322055 A1 | 10/2021 | Lindekugel et al. |
| 2021/0375445 A1* | 12/2021 | Lindekugel ............ H04W 4/38 |
| 2021/0393337 A1* | 12/2021 | Zucker .................... G01L 5/26 |
| 2022/0240976 A1 | 8/2022 | Pett et al. |
| 2022/0249104 A1 | 8/2022 | Pett et al. |
| 2022/0273338 A1* | 9/2022 | Eisenthal .......... A61B 17/3403 |
| 2023/0106545 A1 | 4/2023 | Pett et al. |
| 2023/0285049 A1 | 9/2023 | Howell |
| 2023/0414251 A1* | 12/2023 | Pett .................... A61B 17/1624 |
| 2024/0058036 A1* | 2/2024 | Lindekugel ......... A61B 10/025 |
| 2024/0206887 A1* | 6/2024 | Pett ....................... H02J 7/0042 |
| 2024/0261554 A1* | 8/2024 | Akerele-Ale ...... A61M 39/0247 |
| 2024/0277375 A1* | 8/2024 | Lindekugel ........ A61B 17/3472 |
| 2025/0120743 A1 | 4/2025 | Pett et al. |

FOREIGN PATENT DOCUMENTS

| | | |
|---|---|---|
| EP | 0923961 A1 | 6/1999 |
| EP | 3687024 A1 | 7/2020 |
| ES | 2390297 A1 | 11/2012 |
| FR | 2581548 A1 | 11/1986 |
| JP | 2018509969 A | 4/2018 |
| KR | 20090006621 A | 1/2009 |
| WO | 1997024151 A1 | 7/1997 |
| WO | 1998052638 A3 | 2/1999 |
| WO | 2005/046769 A2 | 5/2005 |
| WO | 05041790 A2 | 5/2005 |
| WO | 2005053506 A2 | 6/2005 |
| WO | 2005072625 A2 | 8/2005 |
| WO | 2007018809 A2 | 2/2007 |
| WO | 2008002961 A2 | 1/2008 |
| WO | 2008016757 A2 | 2/2008 |
| WO | 2008033871 A2 | 3/2008 |
| WO | 2008033872 A2 | 3/2008 |
| WO | 2008033873 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |

(56) References Cited

FOREIGN PATENT DOCUMENTS

| | | | |
|---|---|---|---|
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011070593 A1 | 6/2011 |
| WO | 2011097311 A2 | 8/2011 |
| WO | 2011139294 A1 | 11/2011 |
| WO | 2013003885 A2 | 1/2013 |
| WO | 2013009901 A2 | 1/2013 |
| WO | 2013173360 A1 | 11/2013 |
| WO | 2014075165 A1 | 5/2014 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015061370 A1 | 4/2015 |
| WO | 2015/177612 A1 | 11/2015 |
| WO | 2016033016 A1 | 3/2016 |
| WO | 16053834 A1 | 4/2016 |
| WO | 2016/085973 A1 | 6/2016 |
| WO | 2016163939 A1 | 10/2016 |
| WO | 18006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | 2019051343 A1 | 3/2019 |
| WO | 2019/164990 A1 | 8/2019 |
| WO | 2021/011795 A1 | 1/2021 |
| WO | 2021/016122 A1 | 1/2021 |
| WO | 2021/062385 A1 | 4/2021 |
| WO | 2021062038 A1 | 4/2021 |
| WO | 2021062394 A1 | 4/2021 |
| WO | 2022/165232 A1 | 8/2022 |
| WO | 2022170269 A1 | 8/2022 |
| WO | 2023177634 A1 | 9/2023 |
| WO | 2024163884 A1 | 8/2024 |

OTHER PUBLICATIONS

PCT/US2019/018828 filed Feb. 20, 2019 International Preliminary Report on Patentability dated Aug. 27, 2020.
PCT/US2019/018828 filed Feb. 20, 2019 International Search Report and Written Opinion dated Jun. 13, 2019.
PCT/US2020/053119 filed Sep. 28, 2020 International Search Report and Written Opinion dated Jan. 5, 2021.
PCT/US2020/052558 filed Sep. 24, 2020 International Search Report and Written Opinion dated Feb. 11, 2021.
PCT/US2020/053135 filed Sep. 28, 2020 International Search Report and Written Opinion dated Dec. 18, 2020.
PCT/US2021/035232 filed Jun. 1, 2021 International Search Report and Written Opinion dated Oct. 19, 2021.
PCT/US2021/028114 filed Apr. 20, 2021 International Search Report and Written Opinion dated Jul. 12, 2021.
PCT/US2021/035475 filed Jun. 2, 2021 International Search Report and Written Opinion dated Sep. 17, 2021.
EP 20867024.0 filed Apr. 21, 2022 Extended European Search Report dated Aug. 8, 2023.
EP 20868351.6 filed Apr. 21, 2022 Extended European Search Report dated Aug. 10, 2023.
U.S. Appl. No. 17/235,134, filed Apr. 20, 2021 Notice of Allowance dated Sep. 20, 2023.
U.S. Appl. No. 17/335,870, filed Jun. 1, 2021 Non-Final Office Action dated Nov. 15, 2023.
U.S. Appl. No. 17/337,100, filed Jun. 2, 2021 Final Office Action dated Nov. 21, 2023.
U.S. Appl. No. 17/667,291, filed Feb. 8, 2022 Non-Final Office Action dated Aug. 31, 2023.
U.S. Appl. No. 17/863,898, filed Jul. 13, 2022 Final Office Action dated Nov. 22, 2023.
PCT/US2021/046573 filed Aug. 18, 2021 International Search Report and Written Opinion dated Nov. 30, 2021.
PCT/US2021/047378 filed Aug. 24, 2021 International Search Report and Written Opinion dated Nov. 17, 2021.
PCT/US2021/048542 filed Aug. 31, 2021 International Search Report and Written Opinion dated Dec. 9, 2021.
PCT/US2021/049475 filed Sep. 8, 2021 International Search Report and Written Opinion dated Dec. 9, 2021.
U.S. Appl. No. 17/031,650, filed Sep. 24, 2020 Notice of Allowance dated Oct. 12, 2022.
U.S. Appl. No. 17/035,272, filed Sep. 28, 2020 Non-Final Office Action dated Mar. 9, 2023.
U.S. Appl. No. 17/035,272, filed Sep. 28, 2020 Restriction Requirement dated Dec. 9, 2022.
U.S. Appl. No. 17/035,336, filed Sep. 28, 2020 Notice of Allowance dated Jan. 11, 2023.
U.S. Appl. No. 17/235,134, filed Apr. 20, 2021 Restriction Requirement dated Mar. 7, 2023.
U.S. Appl. No. 17/031,650, filed Sep. 24, 2020 Non-Final Office Action dated Jan. 19, 2022.
PCT/US2022/014391 filed Jan. 28, 2022 International Search Report and Written Opinion dated Apr. 14, 2022.
PCT/US2022/015686 filed Feb. 8, 2022 International Search Report and Written Opinion dated May 25, 2022.
U.S. Appl. No. 17/031,650, filed Sep. 24, 2020 Final Office Action dated Jul. 20, 2022.
U.S. Appl. No. 17/035,336, filed Sep. 28, 2020 Restriction Requirement dated Jul. 26, 2022.
EP 19757657.1 filed Sep. 18, 2020 Extended European Search Report dated Oct. 22, 2021.
EP 23166984.7 filed Apr. 6, 2023 Extended European Search Report dated Jul. 5, 2023.
PCT/US2023/015127 filed Mar. 13, 2023 International Search Report and Written Opinion dated Jun. 26, 2023.
U.S. Appl. No. 17/035,272, filed Sep. 28, 2020 Notice of Allowance dated Jul. 7, 2023.
U.S. Appl. No. 17/235,134, filed Apr. 20, 2021 Non-Final Office Action dated Jun. 27, 2023.
U.S. Appl. No. 17/335,370, filed Jun. 1, 2021 Restriction Requirement dated Jul. 25, 2023.
U.S. Appl. No. 17/337,100, filed Jun. 2, 2021 Non-Final Office Action dated Jun. 2, 2023.
U.S. Appl. No. 17/667,291, filed Feb. 8, 2022 Restriction Requirement dated May 31, 2023.
U.S. Appl. No. 17/405,692, filed Aug. 18, 2021 Non-Final Office Action dated Sep. 6, 2024.
U.S. Appl. No. 17/410,863, filed Aug. 24, 2021 Non-Final Office Action dated Sep. 5, 2024.
U.S. Appl. No. 17/463,324, filed Aug. 31, 2021 Non-Final Office Action dated Oct. 30, 2024.
U.S. Appl. No. 17/463,324, filed Aug. 31, 2021 Restriction Requirement dated Aug. 8, 2024.
U.S. Appl. No. 18/075,269, filed Dec. 5, 2022 Notice of Allowance dated Sep. 11, 2024.
U.S. Appl. No. 18/244,730, filed Sep. 11, 2023 Final Office Action dated Aug. 8, 2024.
U.S. Appl. No. 18/244,730, filed Sep. 11, 2023 Notice of Allowance dated Oct. 24, 2024.
U.S. Appl. No. 18/385,056, filed Oct. 30, 2023 Notice of Allowance dated Aug. 29, 2024.
U.S. Appl. No. 17/335,870, filed Jun. 1, 2021 Final Office Action dated Mar. 26, 2024.
U.S. Appl. No. 17/337,100, filed Jun. 2, 2021 Notice of Allowance dated Jan. 24, 2024.
PCT/US2024/014241 filed Feb. 2, 2024 International Search Report and Written Opinion dated May 8, 2024.
U.S. Appl. No. 17/405,692, filed Aug. 18, 2021 Restriction Requirement dated May 10, 2024.

(56) References Cited

OTHER PUBLICATIONS

U.S. Appl. No. 18/075,269, filed Dec. 5, 2022 Non-Final Office Action dated Jun. 24, 2024.
U.S. Appl. No. 18/244,730, filed Sep. 11, 2023 Non-Final Office Action dated May 3, 2024.
U.S. Appl. No. 18/385,056, filed Oct. 30, 2023 Non-Final Office Action dated May 9, 2024.
U.S. Appl. No. 17/405,692, filed Aug. 18, 2021 Final Office Action dated Dec. 4, 2024.
U.S. Appl. No. 17/410,863, filed Aug. 24, 2021 Notice of Allowance dated Dec. 13, 2024.
U.S. Appl. No. 17/587,900, filed Jan. 28, 2022 Non-Final Office Action dated Nov. 14, 2024.
U.S. Appl. No. 18/599,077, filed Mar. 7, 2024 Non-Final Office Action dated Feb. 3, 2025.
U.S. Appl. No. 17/405,692, filed Aug. 18, 2021 Advisory Action dated Feb. 14, 2025.
U.S. Appl. No. 17/405,692, filed Aug. 18, 2021 Non-Final Office Action dated Apr. 10, 2025.
U.S. Appl. No. 17/463,324, filed Aug. 31, 2021 Final Office Action dated Feb. 18, 2025.
U.S. Appl. No. 17/587,900, filed Jan. 28, 2022 Final Office Action dated Apr. 17, 2025.
U.S. Appl. No. 18/599,077, filed Mar. 7, 2024 Notice of Allowance dated Apr. 16, 2025.

* cited by examiner

ASPIRATION APPARATUS FOR INTRAOSSEOUS ACCESS SYSTEM

PRIORITY

This application claims the benefit of priority to U.S. Patent Application No. 63/076,189, filed Sep. 9, 2020, which is incorporated by reference in its entirety into this application.

BACKGROUND

Intraosseous (IO) access systems are configured to access a medullary cavity of a bone by drilling an access needle through the dense bone cortex and into the medullary cavity. Some IO access systems include a powered drill, or similar device, configured to rotate a needle assembly at high rotational speeds to drill an access needle through the bone cortex. Detecting when the needle has accessed the medullary cavity can be challenging. For example, to confirm access to the medullary cavity, a user must disengage the drill from the needle assembly, withdraw the obturator from a lumen of the needle, attach a syringe to the access needle and aspirate the needle lumen to observe the presence of bone marrow. Failure to aspirate bone marrow may mean that the access needle has not fully accessed the medullary cavity and further drilling is required. However, with the needle assembly disengaged from the drill, and the obturator withdrawn from the needle lumen, the needle cannot be reused and the clinician must withdraw the needle, couple a new needle assembly to the drill, and continue drilling. Further, patency of the original access site may be lost during needle exchange.

Disclosed herein are systems, apparatus and methods directed to address the foregoing problems.

SUMMARY

Disclosed herein is an intraosseous access system including, a housing, a needle assembly extending from a distal end of the housing and including an obturator extending along a longitudinal axis and disposed within a lumen of a needle, an aspiration system disposed within the housing and including one of a syringe or a vacutainer, the aspiration system configured to slide the obturator relative to the needle and selectively provide a vacuum in fluid communication with the needle lumen, and a drive train disposed within the housing and configured to rotate the needle assembly and one of a syringe barrel or a vacutainer canister about the longitudinal axis.

In some embodiments, the drive train includes one of a biasing member, an electric motor, or a battery. In some embodiments, the syringe includes a plunger slidably engaged with the syringe barrel and the housing along a longitudinal axis, the syringe barrel rotatable about the longitudinal axis relative to the plunger. In some embodiments, the intraosseous access system further includes a piston rotatably coupled to one of the plunger, the syringe barrel, or the obturator. In some embodiments, the intraosseous access system further includes a handle coupled to the plunger, a portion of the handle extending through a wall of the housing.

In some embodiments, the vacutainer includes a valve configured to selectively place a vacuum, disposed within the vacutainer canister, in fluid communication with the needle lumen. In some embodiments, the vacutainer further includes an actuator configured to slide the canister along a longitudinal axis or actuate the valve between an open and closed position. In some embodiments, the housing further includes an observation window configured to allow a user to observe one of the syringe barrel or vacutainer canister disposed therebelow. In some embodiments, one of the syringe barrel or vacutainer canister can include a transparent material. In some embodiments, the biasing member is one of a flat spring, a coiled spring, or a torsion spring. In some embodiments, a distal tip of the obturator is configured to be withdrawn into one of the syringe barrel or the housing 104 to mitigate accidental needle stick injuries.

Also disclosed is a method for accessing a medullary cavity including, actuating a drive train disposed within a housing, rotating a needle assembly coupled to the drive train and including an obturator disposed within the a lumen of a needle, the needle extending along a longitudinal axis, rotating one of a syringe barrel or a vacutainer canister relative to the housing about the longitudinal axis, withdrawing an obturator from the needle lumen to provide a fluid communication between the needle lumen and one of the syringe barrel or the vacutainer canister, and replacing the obturator within the needle lumen.

In some embodiments, the drive train includes one of a biasing member, a flat spring, a coiled spring, a torsion spring, an electric motor, or a battery. In some embodiments, the method further includes sliding a handle coupled to one of a plunger or the vacutainer canister along a longitudinal axis relative to the housing, the handle remaining in a rotatably fixed position about the longitudinal axis, relative to the housing. In some embodiments, the handle extends through an aperture disposed in a wall of the housing. In some embodiments, the method further includes rotating a piston coupled to a distal end of the plunger, relative to one of the handle or the syringe barrel, the piston providing a fluid tight seal between a wall of the syringe barrel and the piston.

In some embodiments, the method further includes confirming access to the medullary cavity by observing a fluid flow into one of the syringe barrel or the vacutainer through one or more viewing windows disposed in the housing. In some embodiments, the method further includes detaching the needle from the needle assembly. In some embodiments, the method further includes disposing the obturator within one of the syringe barrel or the vacutainer canister to mitigate needle stick injuries.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
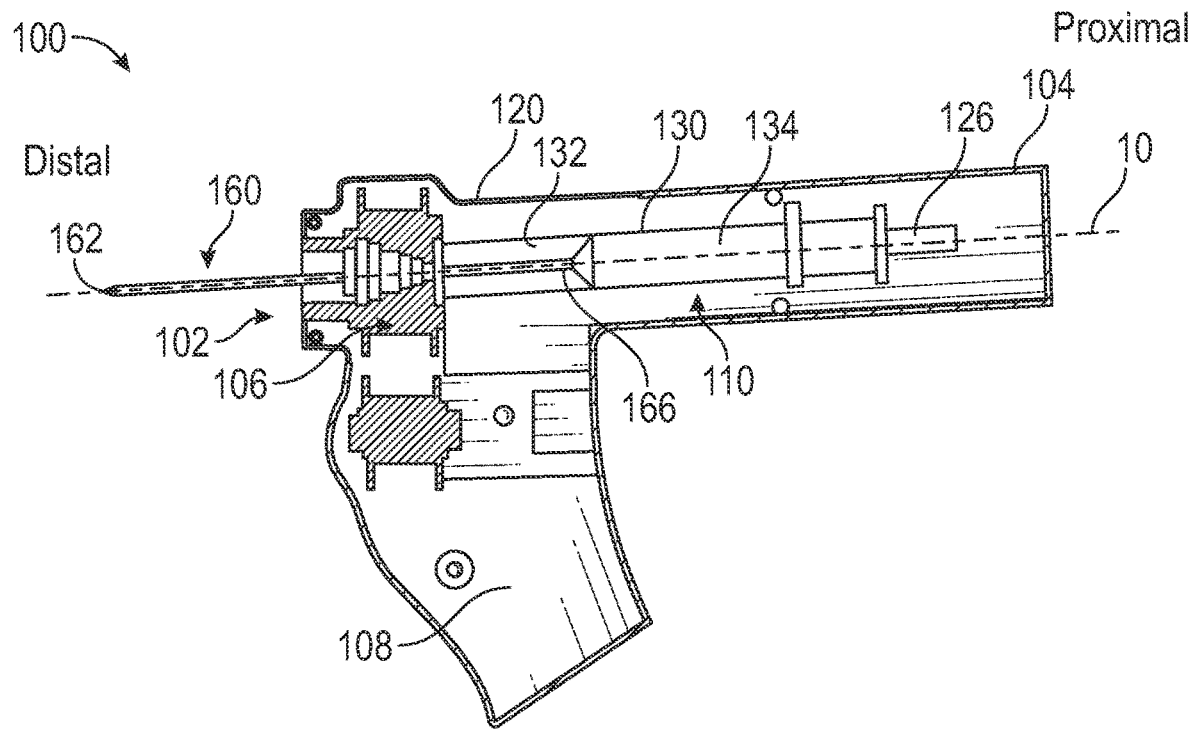
FIG. 1A illustrates a side view of an intraosseous access system including an aspiration system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal-end portion, or the proximal length of the needle can include the proximal end of the needle; however, the proximal portion, the proximal-end portion, or the proximal length of the needle need not include the proximal end of the needle. That is, unless context suggests otherwise, the proximal portion, the proximal-end portion, or the proximal length of the needle is not a terminal portion or terminal length of the needle.

With respect to "distal," a "distal portion" or a "distal-end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal-end portion, or the distal length of the needle can include the distal end of the needle; however, the distal portion, the distal-end portion, or the distal length of the needle need not include the distal end of the needle. That is, unless context suggests otherwise, the distal portion, the distal-end portion, or the distal length of the needle is not a terminal portion or terminal length of the needle.

Unless defined otherwise, all technical and scientific terms used herein have the same meaning as commonly understood by those of ordinary skill in the art.

Figure 1B:
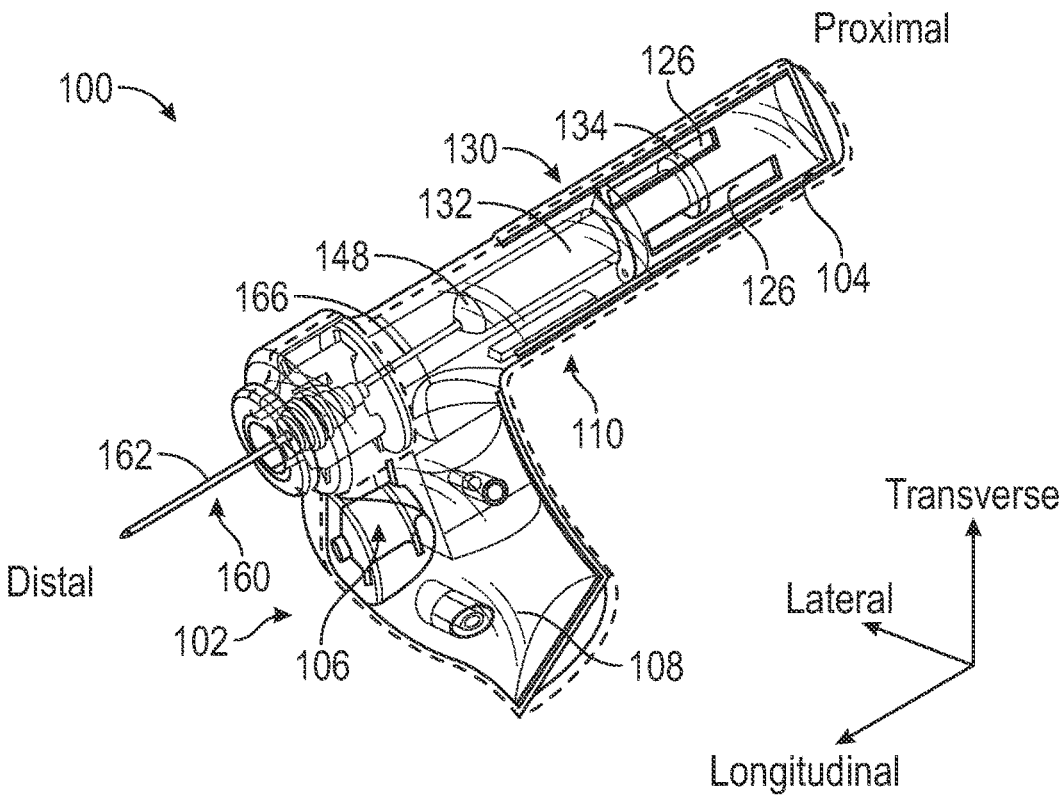
FIG. 1B illustrates a perspective view of an intraosseous access system including an aspiration system, in accordance with some embodiments.

FIG. 1A illustrates a side view of an intraosseous (IO) access system ("system") 100 including an aspiration system 110, in accordance with some embodiments. FIG. 1B illustrates a perspective view of an intraosseous access system 100 with portions thereof shown in wire frame.

The system 100 can generally include an access system 102 and an aspiration system 110. The access system 102 can include a drive train 106 coupled to a needle assembly 160. The drive train 106 can be configured to rotate the needle assembly 160 and drill a needle 162 through a bone cortex to access a medullary cavity. The aspiration system 110 can be in fluid communication with a needle 162 of the needle assembly 160 and can confirm access to the medullary cavity by aspirating bone marrow through a needle lumen 164. Advantageously, the intraosseous access system 100 can be configured to determine when the medullary cavity has been accessed by aspirating the needle 162 without disengaging the needle assembly 160 from the system 100.

In an embodiment, the intraosseous access system 100 can include a housing 104 including one or more of the access system 102, the aspiration system 110, or portions thereof, disposed therein. The access system 102 can include a needle assembly 160 rotatably coupled to the drive train 106 and extending from a distal end of the housing 104. Optionally, the housing 104 can include a grip, e.g. a pistol grip 108, or similar structures, configured to facilitate grasping the housing 104 and urging the needle 162 distally into a bone.

In an embodiment, the drive train 106 of the access system 102 can be configured to provide rotational movement to one or both of the aspiration system 110 and the needle assembly 160, as described in more detail herein. In some embodiments, the access system 102 can be an automated driver (e.g. a drill that achieves high rotational speeds). In an embodiment, the access system 102 can be an automated driver that includes a drive train 106 having an electrical energy source (e.g. battery) to provide electrical power to a drilling mechanism, e.g. an electric motor, or the like. In an embodiment, the system 100 can include an actuator, e.g. button, switch, or the like, configured to actuate the drive train 106. In an embodiment, the drive train 106 can be actuated by an axial pressure applied to a distal tip of the needle 162.

In an embodiment, the drive train 106 can include a spring powered drilling mechanism, e.g. a coiled spring, flat spring, torsion spring, or similar biasing member, which may store potential mechanical energy and may be released upon actuation of the drive train 106. In an embodiment, the drive train 106 can further include one or more gear mechanisms, biasing members, bearings, bushings, or the like, configured to facilitate rotating the needle assembly 160. In an embodiment, the access system 102 can be a manual driver where a clinician can use a handle, pistol grip 108, or similar structure to urge the needle assembly 160 through the bone cortex.

In an embodiment, a portion of the housing 104 can include the aspiration system 110 disposed therein. The housing 104 can include one or more viewing windows 120 configured to allow a user to observe a portion of the aspiration system 110 disposed therein. In an embodiment, the viewing window 120 can define an aperture extending through a wall of the housing 104. In an embodiment, the viewing window 120 can include a transparent or translucent portion of the housing 104. In an embodiment, the entire housing 104 can be formed of a translucent or transparent material configured to allow a user to observe one or both of the aspiration system 110 and the access system 102, or portions thereof, disposed therein.

Figure 2:
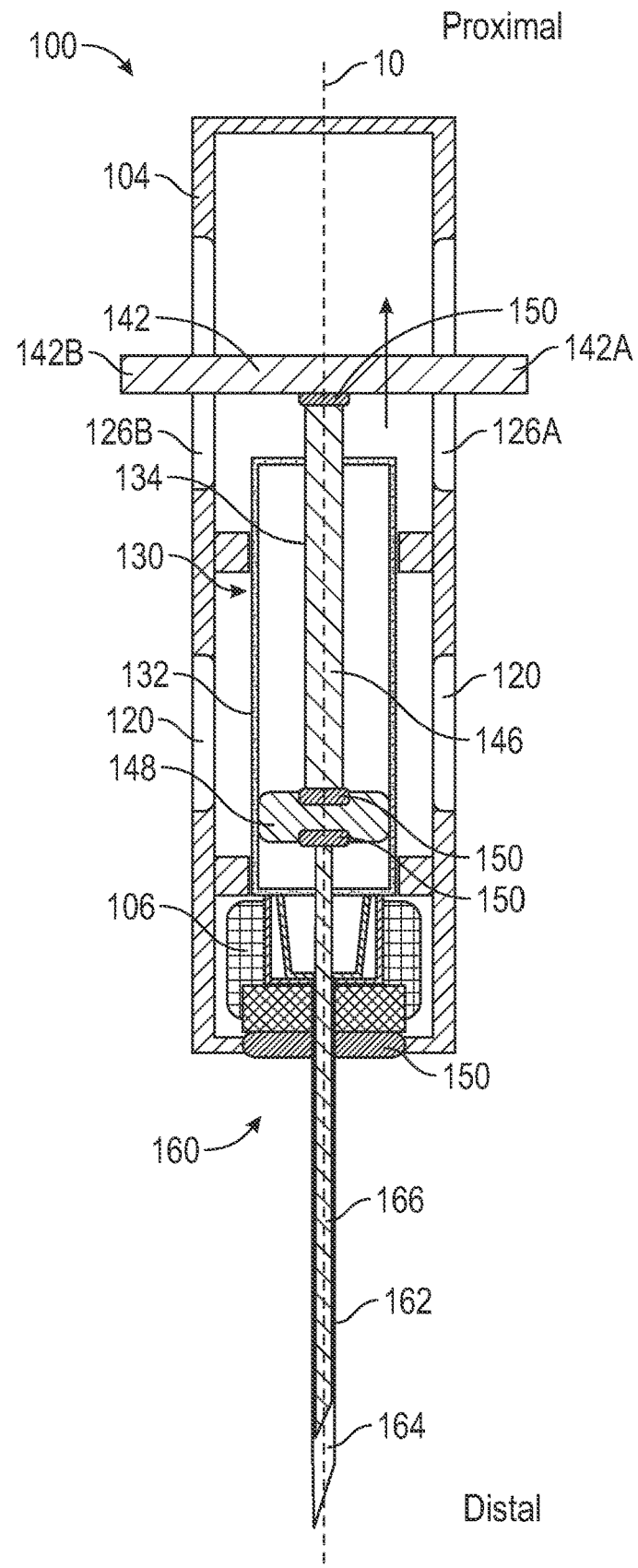
FIG. 2 illustrates a plan, cross-section view of an intraosseous access system including an aspiration system having a syringe, in accordance with some embodiments.

As shown in FIGS. 1A-2, in an embodiment, the aspiration system 110 can include a syringe 130 having a barrel 132, and a plunger 134 slidably engaged therewith. The barrel 132 can be in fluid communication with a lumen 164 of the needle 162. Sliding the plunger 134 relative to the barrel 132 can create a vacuum within the barrel 132 and can draw a fluid flow through the needle lumen 164 and into the barrel 132. In an embodiment, a portion of the barrel 132 can be formed of a translucent or transparent material. In use, a user can observe the fluid flow within the syringe barrel 132 through one of the viewing windows 120.

In an embodiment, the aspiration system 102 can include a vacutainer, or similar structure configured to maintain a vacuum therein, as described in more detail herein. In use, a user can actuate a release mechanism, e.g. actuator, valve, etc., to place the vacutainer in fluid communication with the needle lumen 164 and draw a fluid flow into the vacutainer. A portion of the vacutainer can be formed of a transparent or translucent material, configured to allow a user to observe a fluid flow, as described herein.

In an embodiment, the aspiration system 110 can be coupled to the access system 102, or portions thereof. In an embodiment, the aspiration system 110 can be coupled to the needle assembly 160, or portions thereof. In an embodiment, one or both of the aspiration system 110 and the needle assembly 160 can be rotatable relative to the housing 104. In an embodiment, the drive train 106 can be configured to rotate the needle assembly 160 and aspiration system 102 assembly about a central longitudinal axis 10.

In an embodiment, a distal end of the syringe barrel 132 can be coupled with the access system 102, or the needle assembly 160, or both. In an embodiment, a distal end of the syringe barrel 132 can be integrally formed with the access system 102. In an embodiment, a distal end of the syringe barrel 132 can be selectively coupled with the access system 102 using a threaded engagement system, an interference fit, press-fit, snap-fit engagement, luer lock, combinations thereof, or the like. In an embodiment, a distal end of the syringe barrel 132 can be coupled with the access system 102 using adhesive, bonding, welding, or the like.

In an embodiment, the syringe barrel 132 can be coupled with the needle assembly 160 and the drive train 106 and can rotate both the barrel 132 and the needle assembly 160 about a central longitudinal axis 10 relative to the housing 104. Further, the plunger 134 can remain substantially stationary relative to the housing 104 with regards to any rotational movement about the central longitudinal axis 10. To note, the plunger 134 may still be slidably engaged with the syringe barrel 132 parallel to a longitudinal axis. Further, the plunger 134 can also be slidable along the longitudinal axis 10 relative to the housing 104.

In an embodiment, the needle assembly 160 can include an obturator 166 disposed within a needle lumen 164 and configured to prevent tissue and bone fragments from entering and occluding the needle lumen 164. A proximal end of the obturator 166 can be coupled to the plunger 134. In an embodiment, the obturator 166 can be rotatable relative to the plunger 134. For example, the obturator 166 can be coupled to the plunger 134 using a bearing 150. As used herein a bearing 150 can include a ball-bearing, bushing, or similar structure configured to facilitate rotational movement about an axis. As such, as the needle assembly 160, including the needle 162 and the obturator 166, is rotated by the drive train 106, the obturator 166 can rotate relative to the plunger 134. Further, sliding the plunger 134 longitudinally, relative to the housing 104, can slide the obturator 166 relative to the needle 162.

In use, rotating the needle assembly 160 can drill a needle 162 through a bone cortex and access the medullary cavity. In an embodiment, once the user believes the medullary cavity has been accessed, the plunger 134 can be withdrawn proximally to both create a vacuum within the barrel 132 and remove the obturator 166 from the needle lumen 164 to place the barrel 134 in fluid communication with the needle lumen 164. If access to the medullary cavity has been achieved, bone marrow can be aspirated through the needle lumen 164. A user can visualize bone marrow in the syringe barrel 132 through the one or more viewing windows 120 to confirm access to the medullary cavity has been achieved. Advantageously, the aspiration system 110 allows for confirmation of access to the medullary cavity by bone marrow aspiration without the need to disassemble the needle assembly 160 from the intraosseous access system 100. In the event that access to the medullary cavity has not been achieved, i.e. no bone marrow is observed, the user can advance the plunger 134 distally, replacing the obturator 166 within the needle lumen 164 and continue drilling the needle assembly 160 through the bone cortex.

FIG. 2 illustrates a plan, cross-section view of an intraosseous access system 100. In some embodiments, the one or more viewing windows 120 can be located on a distal portion of the housing body 112 and can be configured to allow a user to observe aspiration of fluids from the needle lumen 164.

In some embodiments, the plunger 132 can include a plunger shaft 146 extending longitudinally through a portion of the syringe barrel 134. A proximal end of the plunger shaft 146 can be coupled to a plunger handle 142 extending perpendicular thereto. In an embodiment, the plunger handle 142 can be rotatably coupled to the plunger shaft 146 and can include a bearing 150, disposed therebetween. As such, in an embodiment, the drive train 106 can rotate one or more of the needle assembly 160, syringe barrel 132, and plunger shaft 146 about the central longitudinal axis 10, and the handle 142 can remain substantially stationary with regards to any rotational movement. In an embodiment, a portion of the plunger handle 142, e.g. a first portion 142A and a second portion 142B, can extend from the plunger shaft 146 perpendicular to a longitudinal axis. In an embodiment, a portion of the plunger handle 142 can extend from the plunger shaft 146 perpendicular to a longitudinal axis to contact a wall of the housing 104.

In an embodiment, a portion of the plunger handle 142 can extend from the plunger shaft 146 perpendicular to a longitudinal axis and extend through a housing aperture 126 disposed in a wall of the housing 104. In an embodiment, a portion of the plunger handle 142 can engage the housing aperture 126 and stabilize the plunger 134 relative to the housing 104, e.g. prevent the handle 142 from rotating relative to the housing 104 about the longitudinal axis 10. For example, a first portion 142A can extend through a first housing aperture 126A and a second portion 142B can extend through a second housing aperture 126B. In an embodiment, the housing aperture 126 can define an elongate shape extending longitudinally. In use a user can grasp a portion of the plunger handle 142, extending through the housing aperture 126 and can urge the plunger 134 longitudinally relative to the housing 104.

In an embodiment, a distal end of the plunger shaft 146 can be coupled to a piston 148. The piston 148 can be formed of a compliant material, e.g. rubber or the like, and can engage an inner surface of the barrel 132 to provide a fluid tight seal therebetween. In use, withdrawing the plunger 134 proximally, along a longitudinal axis can create a vacuum between a proximal surface of the piston 148 and a distal end of the barrel 132.

In an embodiment, the piston 148 can be rotatably coupled to the plunger shaft 146 by way of a bearing 150, bushing, or similar structure. In use, the drive train 106 can rotate the needle assembly 160, the syringe barrel 132 and the piston 148 about the longitudinal axis 10 while the plunger shaft 146 and the housing 104 can remain rotationally stationary relative to the longitudinal axis 10.

In an embodiment, the piston 148 can be in a fixed relationship relative to the plunger shaft 146. The piston 148 can then be rotatable relative to the syringe barrel 134 while maintaining a fluid tight seal therebetween. In use, the drive train 106 can rotate the needle assembly 160 and the syringe barrel 132 about the longitudinal axis 10 while the plunger shaft 146, the piston 148, and the housing 104 can remain rotationally stationary relative to the longitudinal axis 10.

In an embodiment, an obturator 166 can be disposed within the needle lumen 164. A proximal end of the obturator 166 can be coupled to the piston 148 of the plunger 134. In some embodiments, the obturator 166 can be coupled to the piston 148 by a snap-fit, press-fit, or interference fit engagement, or the like, or by adhesive, welding, bonding, combinations thereof, or the like. In an embodiment, the obturator 166 can be coupled in a fixed relationship relative to the plunger 134. In an embodiment, the obturator 166 can be rotatably coupled to the plunger 134 by way of a bearing 150, bushing, or similar structure. As such, the obturator can rotate independently of the piston 148.

In some embodiments, the obturator 166 can be removed from the needle lumen 164 to provide fluid communication, through the needle lumen 164 and into the syringe barrel 132. In an embodiment, withdrawing the plunger 134 can simultaneously generate a vacuum within the syringe barrel 132 and remove the obturator 166 at least partially from the needle lumen 164.

In some embodiments, where no fluid flow is observed, the plunger 134 can be advanced distally and the obturator 166 can be replaced back into the needle lumen 164. In an embodiment, the vacuum within the syringe barrel 132 can facilitate advancing the obturator 166 distally, replacing the obturator 166 back into the needle lumen 164. The obturator 166 can then continue to prevent occlusion of the needle lumen 164 as the needle assembly 160 continues to penetrate the bone cortex. Advantageously, the obturator 166 can be withdrawn from the needle 162 and into the barrel 132 of the syringe 130. As such the barrel 132 can prevent accidental needle stick injuries by the distal end of the obturator 166.

In an embodiment, the drive train 106 can provide rotational movement to the needle assembly 160 in a variety of ways. For example, with the aspiration system 110 being coupled to the needle assembly 160, the drive train 106 can rotate both the aspiration system 110 and the needle assembly 160. In some embodiments, the drive train 106 may rotate only the needle assembly 160, i.e. without rotating the aspiration system 110. In some embodiments, the drive train 106 may rotate one or more components of the aspiration system 110 and/or needle assembly 160 while maintaining other components stationary relative thereto.

In an embodiment, the drive train 106 can rotate the barrel 132 of the syringe 130 while maintaining the plunger 134 stationary relative to any rotation about the longitudinal axis 10. In an embodiment, the plunger handle 142 can engage the housing aperture 126 to prevent the plunger 134 from rotating about the longitudinal axis 10 as the barrel 132 rotates. In an embodiment, the plunger shaft 146 may be coupled to a bearing 150 bushing, or the like, disposed within the piston 148. The bearing 150 is configured to allow rotational movement of piston 148 around the central axis 10 while allowing the plunger shaft 146 to remain substantially stationary. In some embodiments, the syringe 130 is configured to receive a volume of fluid therein. In some embodiments, the capacity of the syringe maybe between 1 ml and 10 ml. It will be appreciated that other volumes of capacity are also considered.

Figure 3:
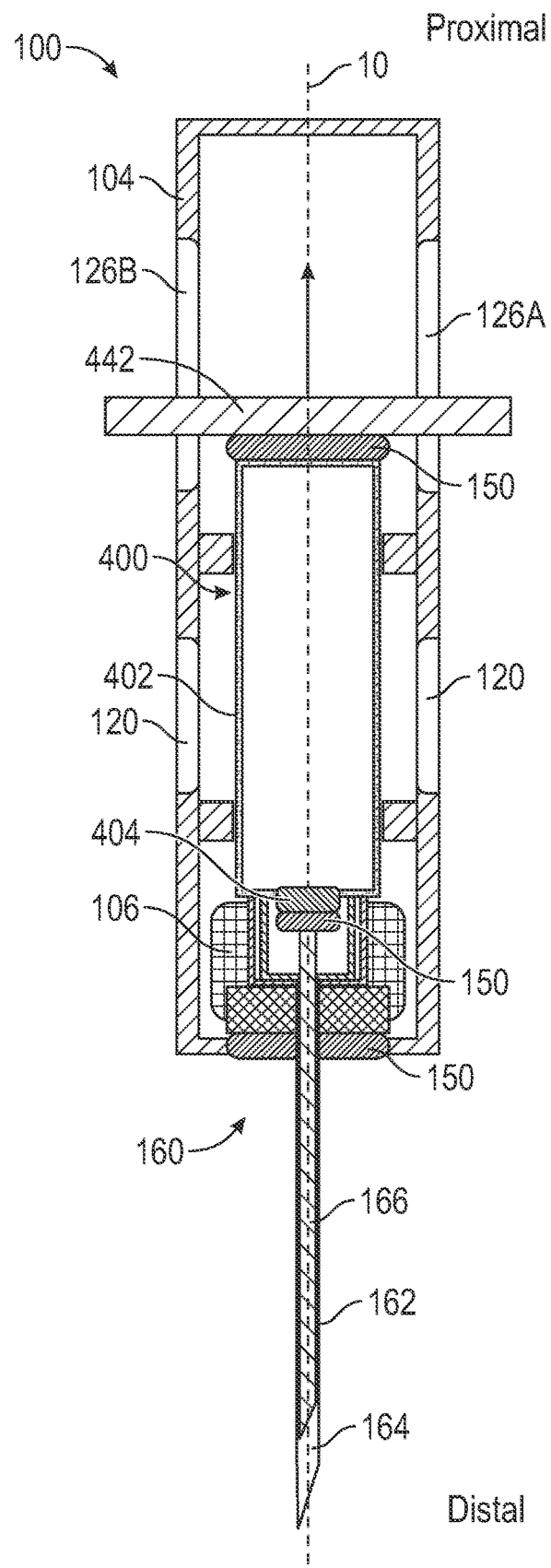
FIG. 3 illustrates a plan, cross-section view of an intraosseous access system including an aspiration system having a vacutainer, in accordance with some embodiments.

FIG. 3 illustrates further details of an embodiment of an intraosseous access system 100 including an aspiration system 110 having a vacutainer 400. The aspiration system 110 can be coupled to the access system 102, as described herein. In an embodiment, the aspiration system 110 can include a vacutainer 400 configured to maintain a vacuum therein. The vacutainer 400 can include a canister 402 configured to maintain a vacuum therein, and a valve 404 configured to control fluid communication between the needle lumen 164 of the needle assembly 160 and the canister 402 vacutainer 400.

In an embodiment, the vacutainer 400 can further include a handle 442. In an embodiment, a portion of the handle 442 can extend through a housing aperture 126, as described herein. In user, a user can grasp the handle 442 and slide the vacutainer 400 longitudinally relative to the housing 104. In an embodiment, the vacutainer 400 can include a bearing 150, bushing, or the like, configured to allow the canister 402 to rotate relative to the handle 442. In an embodiment, a proximal end of the obturator 166 can be coupled a distal end of the vacutainer 400. In an embodiment, the vacutainer can further include a bearing 150 configured to allow the obturator 166 to rotate relative to the vacutainer 400, or portions thereof, e.g. the canister 402 or valve 404.

In an embodiment, the drive train 106 can rotate the vacutainer 400 and the needle assembly 160 about the central axis 10. When the user believes the medullary cavity has been accessed, a user can grasp the handle 442 and slide the vacutainer 400 proximally to at least partially withdraw the obturator 166 from the needle lumen 164 of the needle. With the obturator 166 withdrawn, a user can actuate the valve 404 and provide fluid communication between the needle lumen 164 and the canister 402 of the vacutainer 400. The vacuum within the canister 402 can then draw a fluid flow through the needle lumen 164. In an embodiment, a portion of the canister 402 can be formed of a transparent material and a fluid flow within the canister 402 can be observed through one or more observation windows 120.

If the medullary cavity has been accessed, the user can observe bone marrow within the canister 402. If the medullary cavity has not been accessed, e.g. a distal tip of the needle 162 is still disposed within the bone cortex, no bone marrow will be observed. As such, a user can close the valve 404 and slide the handle 442 distally to replace the obturator 166 within the needle lumen 162 and continue drilling the needle assembly 160 through the bone cortex. Advantageously, withdrawing the vacutainer 400 and obturator 166 assembly proximally can maintain a tip of the obturator 166 within the housing 104 and mitigate accidental needle stick injuries. In an embodiment, the handle 442 can be configured to slide the vacutainer 400 along a longitudinal axis and actuate the valve 404. In an embodiment, a separate actuator can be configured to actuate the valve 404 and transition the valve 404 between an open and a closed position.

In some embodiments, portions of the aspiration system 110 may be configured to be selectively detachable from the access system 102. For example, in an embodiment, in the aspiration system 110, the syringe 130, the vacutainer 400, or combinations thereof may be configured to be detachable and interchangeable. In an embodiment, sliding the syringe 130 or the vacutainer 400 can be achieved by manually operating and handle, as described herein. In an embodiment, the system 100 can further include a second drive train configured to be actuated by a user and slide the aspiration system 110, or portions thereof, along a longitudinal axis.

Figure 4:
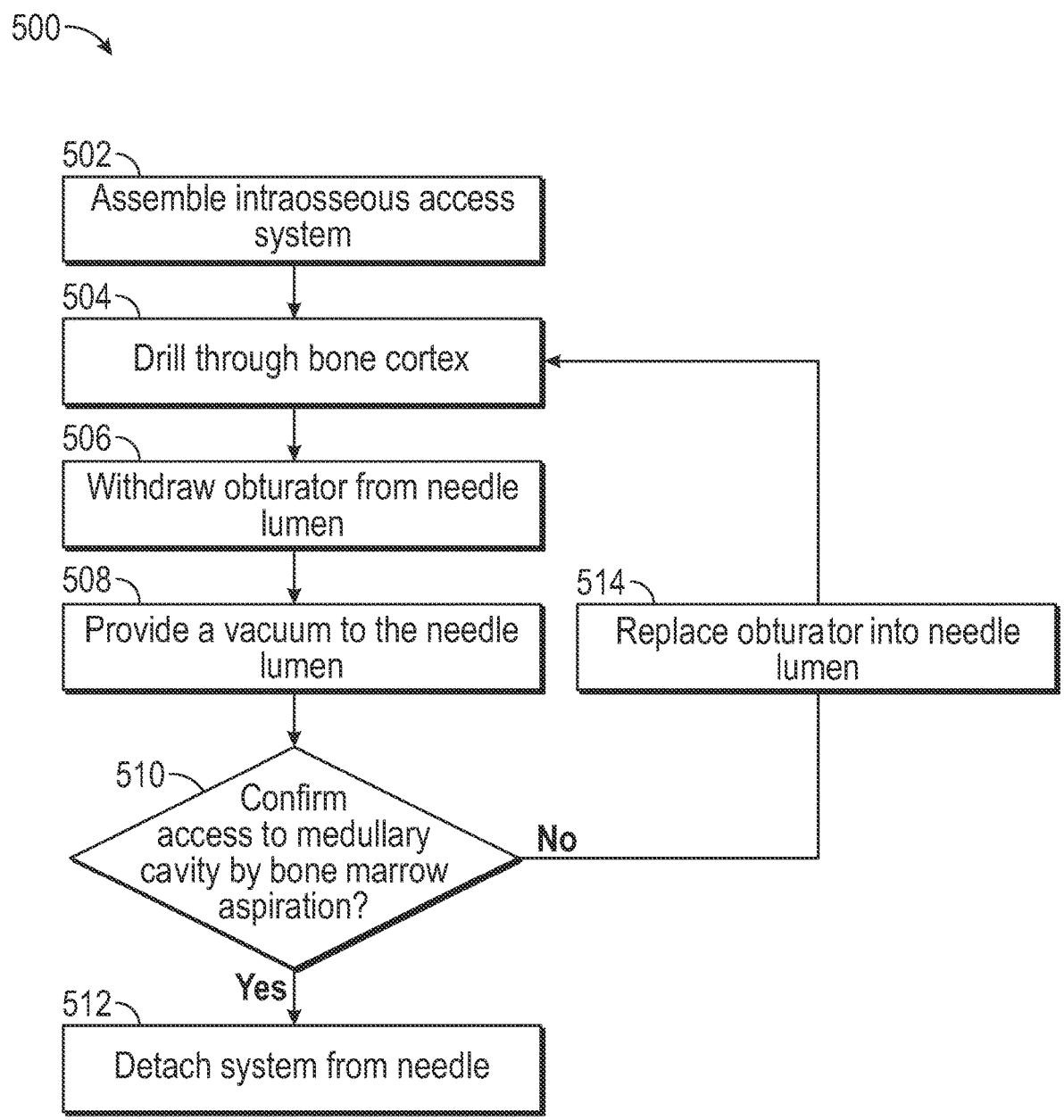
FIG. 4 illustrates a flow chart of an exemplary method of use for an intraosseous access system, in accordance with some embodiments.

FIG. 4 illustrates an exemplary method of use 500 for intraosseous access system 100, including an aspiration system 110. In an embodiment, the method 500 includes assembling the intraosseous access system 100 (block 502). In some embodiments, assembling the intraosseous access system 100 includes coupling a needle assembly 106 with an access system 102 of the system 100. The needle assembly 160 rotatably coupled to the system 100. In some embodiments, assembling the intraosseous access system 100 includes coupling an aspiration system 110 having a syringe 130 or a vacutainer 400 with the system 100.

In an embodiment, the method 500 includes actuating the access system 102 to rotate the needle assembly 160, the aspiration system 110, or components thereof, to drill a needle 162 through a bone cortex to access the medullary cavity (block 504). In an embodiment, when a user believes the medullary cavity has been accessed, the user can confirm access to the medullary cavity by withdrawing the obturator 166 from a needle lumen 164 (block 506). A fluid flow can be drawn through the needle lumen 164 by providing a vacuum in fluid communication with the needle lumen 164 (block 508). The vacuum can be provided either by withdrawing a plunger 134 from a syringe barrel 132, or by actuating a valve to place a vacutainer 400 in fluid communication with the needle lumen 164, or combinations thereof. (block 508).

In an embodiment, the user can then determine if the medullary cavity has been accessed by observing a fluid flow (block 510). If medullary cavity access has been confirmed, the user can detach the system 100 from the needle 162 (block 512). If medullary cavity access is not confirmed, the user replace the obturator 166 within the needle lumen 164 (block 514) and continue drilling through the bone cortex (return to block 504).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An intraosseous access system, comprising:
    a housing;
    a needle assembly including a needle extending from a distal end of the housing along a longitudinal axis, and an obturator disposed within a lumen of the needle;
    an aspiration system disposed within the housing and including one of a syringe or a vacutainer, a proximal end of the obturator coupled to the aspiration system, the aspiration system configured to engage and slide the obturator relative to the needle, the aspiration system further configured to provide a vacuum to the lumen of the needle while remaining engaged with the obturator; and
    a drive train disposed within the housing and configured to rotate the needle assembly and one of a syringe barrel or a vacutainer canister about the longitudinal axis.

2. The intraosseous access system according to claim 1, wherein the drive train includes one of a biasing member, an electric motor, or a battery.

3. The intraosseous access system according to claim 1, wherein the syringe includes a plunger slidably engaged with the syringe barrel and the housing along the longitudinal axis, the syringe barrel rotatable about the longitudinal axis relative to the plunger.

4. The intraosseous access system according to claim 3, further including a piston rotatably coupled to one of the plunger, the syringe barrel, or the obturator.

5. The intraosseous access system according to claim 3, further including a handle coupled to the plunger, a portion of the handle extending through a wall of the housing.

6. The intraosseous access system according to claim 1, wherein the vacutainer includes a valve configured to control fluid communication between the vacutainer canister and the lumen of the needle to selectively apply the vacuum to the lumen of the needle.

7. The intraosseous access system according to claim 6, wherein the vacutainer further includes an actuator configured to slide the vacutainer canister along the longitudinal axis or to actuate the valve between an open and closed position.

8. The intraosseous access system according to claim 1, wherein the housing further includes an observation window configured to allow a user to observe one of the syringe barrel or the vacutainer canister disposed therebelow.

9. The intraosseous access system according to claim 1, wherein one of the syringe barrel or the vacutainer canister can include a transparent material.

10. The intraosseous access system according to claim 2, wherein the biasing member is one of a flat spring, a coiled spring, or a torsion spring.

11. The intraosseous access system according to claim 1, wherein a distal tip of the obturator is configured to be withdrawn into one of the syringe barrel or the housing to mitigate accidental needle stick injuries.

\* \* \* \* \*